United States Patent
Gemeinhart

(10) Patent No.: US 8,414,879 B2
(45) Date of Patent: Apr. 9, 2013

(54) SUPERPOROUS HYDROGEL WITH CELLS ENCAPSULATED THEREIN AND METHOD FOR PRODUCING THE SAME

(75) Inventor: Richard A. Gemeinhart, Chesterton, IN (US)

(73) Assignee: The Board of Trustees of the University of Illinois, Chicago, IL (US)

( * ) Notice: Subject to any disclaimer, the term of this patent is extended or adjusted under 35 U.S.C. 154(b) by 489 days.

(21) Appl. No.: 12/464,340

(22) Filed: May 12, 2009

(65) Prior Publication Data

US 2009/0291115 A1    Nov. 26, 2009

Related U.S. Application Data

(60) Provisional application No. 61/054,624, filed on May 20, 2008.

(51) Int. Cl.
*A01N 63/00* (2006.01)
*A61K 9/00* (2006.01)

(52) U.S. Cl. ........................ 424/93.1; 424/486

(58) Field of Classification Search .................. None
See application file for complete search history.

(56) References Cited

U.S. PATENT DOCUMENTS

| | | | |
|---|---|---|---|
| 5,750,585 A | 5/1998 | Park et al. | 521/143 |
| 2006/0257378 A1 | 11/2006 | Crumpler et al. | 424/93.7 |
| 2008/0089940 A1 * | 4/2008 | Omidian et al. | 424/487 |
| 2008/0193536 A1 | 8/2008 | Khademhosseini | 424/486 |

FOREIGN PATENT DOCUMENTS

WO    WO 00/61668    * 10/2000

OTHER PUBLICATIONS

Gemeinhart et al., "Pore structure of superporous hydrogels", Polym. Adv. Technol. 2000 11:617-625.
Gemeinhart et al., "pH-sensitivity of fast responsive superporous hydrogels", J. Biomater. Sci. Polymer Edn. 2000 11(12):1371-1380.

* cited by examiner

*Primary Examiner* — Nashaat Nashed
(74) *Attorney, Agent, or Firm* — Licata & Tyrrell P.C.

(57) ABSTRACT

The present invention is a superporous hydrogel with cells encapsulated within the hydrogel matrix, and a method for producing the same.

11 Claims, No Drawings

SUPERPOROUS HYDROGEL WITH CELLS ENCAPSULATED THEREIN AND METHOD FOR PRODUCING THE SAME

INTRODUCTION

This application claims benefit of priority from U.S. Provisional Patent Application Ser. No. 61/054,624, filed May 20, 2008, the content of which is incorporated herein by reference in its entirety.

BACKGROUND OF THE INVENTION

Regenerative medicine aims to restore, maintain or improve function of damaged organs. Regenerative medicine bridges the gap between artificial devices and natural organs by providing biological scaffolds, which not only sustain the function of the diseased organ but also accelerate the process of regeneration. The choice of scaffold material and architecture are key to successful regeneration. Natural as well as synthetic scaffolds are routinely employed. Natural materials such as polypeptides, polysaccharides, nucleic acids, hydroxyapatites, or their composites offer excellent physiological activities such as selective cell adhesion (e.g., collagen and fibrin), mechanical properties similar to natural tissues (e.g., animal heart valves and blood vessels), and biodegradability (e.g., gelatin and chitin). However, biological materials have several disadvantages including risk of viral infection, antigenicity, unstable material supply, and deterioration, which accompanies long-term implantation. In addition, naturally-derived materials offer limited versatility in designing an exogenous extracellular matrix with specific properties (e.g., porosity and mechanical strength). Synthetic materials, by contrast, can be manufactured reproducibly on a large scale, and can also be processed into an exogenous extracellular matrix in which the macrostructure, mechanical properties, and degradation time can be readily controlled and manipulated. Exogenous extracellular matrices fabricated by biodegradable polymers eventually break down in the body, avoiding chronic foreign-body responses (Rosso, et al. (2005) *J. Cell. Physiol.* 203:465-70).

An ideal scaffold provides a three dimensional shape for cells to attach and a porous architecture (Bryant & Anseth (2001) *J. Biomed. Mat. Res. A* 59:63-72). In addition, the scaffold should be biodegradable, biocompatible and not elicit an immune response or rejection when implanted in the body. Poly (lactic acid) (PLA), poly(glycolic acid) (PGA), and their copolymers poly(lactic acid-co-glycolic acid) (PLGA) are routinely used as polymers for scaffold designing because of their wide biodegradability and biocompatibility (Chen & Ma (2006) *Biomaterials* 27:3708-15). Moreover, co-polymerization of polyethylene glycol (PEG) with PLA and PLGA has been used to increase the biodegradability of PEG (Bryant, et al. (2004) *Biotechnol. Bioeng.* 86:747-55).

Scaffolds can be classified into two categories based on their porosity, non-porous scaffolds (Fukuda, et al. (2006) *Biomaterials* 27:5259-67) and porous scaffolds (Norman & Desai *Ann. Biomed. Eng.* 34:89-101). Commonly used methods for creating unordered porous structures include polymer demixing (Dalby, et al. (2002) *Tissue Eng.* 8:1099-108), phase separation (Smith & Ma (2004) supra), foaming (Chen, et al. (1999) *J. Biomed. Mater. Res.* 44:53-62), colloidal lithography (Dalby, et al. (2004) *Biomaterials* 25:5415-22; Denis, et al. (2004) *Langmuir* 20:9335-9), self-assembly (Tu & Tirrell (2004) *Adv. Drug Deliv. Rev.* 56:1537-63), chemical etching (Tu & Tirrell (2004) supra; Thapa, et al. (2003) *Biomaterials* 24:2915-26), and thermogellation (US Patent Application No. 20060257378). Ordered structures can also be obtained by photolithography, electron beam lithography (Curtis, et al. (2001) *Biophys. Chem.* 94:275-83; Smith & Ma (2004) *Colloids Surf. B Biointer.* 39:125-31), and electrospinning (Williams, et al. (2005) *Biomaterials* 26:1211-8; Jayaraman, et al. (2004) *J. Nanosci. Nanotechnol.* 4:52-65). In addition, US Patent Application No. 20080193536 discloses microfabrication of cell-laden hydrogels using soft lithographic techniques. However, macroscopic, non-porous hydrogels, prepared for example by photopolymerization techniques, have the disadvantages of photoinitiator toxicity (Williams, et al. (2005) *Biomaterials* 26:1211), limited diffusion, and limited cell-cell interactions within the scaffolds (Nuttelman, et al. (2004) *J. Biomed. Mater. Res. A* 68:773).

In comparison, porous scaffolds with a pore size of greater than 100 μm are reported to promote bone ingrowth within the pores of the scaffolds (Langer & Vacanti (1993) *Science* 260:920) and promote cell-cell interactions. Insufficient interconnectivity in biodegradable hydrophobic polymers, e.g., poly(lactide-co-glycolide) copolymers, has been shown to be the limiting factor in cell colonization and new tissue formation (Crane, et al. (1995) *Nat. Med.* 1:1322; Ishaug, et al. (1997) *J. Biomed. Mater. Res.* 36:17). Microchannel conduits have been engineered in non-porous PEGDA hydrogels for generating vascularized adipose tissue grafts (Stosich, et al. (2007) *Tissue Eng.* 13:2881). This study highlighted the necessity of a porous scaffold structure for vascularization. The presence of interconnected pores within the scaffold was shown to enable vascular capillary ingrowth from the host tissue into the interconnected network of the scaffold (Hutmacher (2000) *Biomaterial* 21:2529).

One of the limiting factors of hydrogels has been the rather slow swelling property of dried hydrogels. For the dried hydrogels to swell, water has to be absorbed into the glassy matrix of the dried hydrogels. The swelling kinetics of the dried hydrogels thus depend on the absorption of water occurring by a diffusional process and the relaxation of the polymer chains in the rubbery region. Equilibrium swelling of dried hydrogels in an ordinary tablet size (e.g., 1 cm in diameter× 0.5 cm height) usually takes at least several hours, and this may be too slow for many applications where fast swelling is essential. Superporous hydrogels (SPHs) are a class of macroporous hydrogels developed for fast-swelling applications (Gemeinhart, et al. (2000) *Polymers Adv. Technol.* 11:617). SPHs can be prepared from addition monomers, such as PEGDA, by a gas foaming technique wherein the foaming and gelation processes are simultaneous to yield hydrogels with a macroporous network. The gas foaming technique is carried out by adding macromer, initiator, and foam stabilizer to a tube; acidifying this solution to retard the polymerization process; and subsequently adding sodium bicarbonate to generate carbon dioxide bubbles, which makes the foam rise. The addition of sodium bicarbonate increases the pH, resulting in faster polymerization of macromers. Due to this methodology, SPHs have a highly porous interconnected structure and large surface-to-volume ratio throughout the scaffold (Gemeinhart, et al. (2000) supra).

SUMMARY OF THE INVENTION

The present invention features a superporous hydrogel with cells encapsulated therein and a method for producing the same. The method of the invention involves combining cells with a hydrogel precursor solution and adding a foaming agent thereby producing a superporous hydrogel with cells encapsulated therein. In some embodiments, the hydrogel precursor solution comprises a synthetic hydrophilic polymer such as poly(ethylene glycol)diacrylate. In other embodiments, the hydrogel precursor solution comprises a foam stabilizer such as a (poly(ethylene oxide)-poly(propylene oxide)-poly(ethylene oxide) tri-block copolymer. In certain embodiments, the foaming agent is a physical or chemical foaming agent. According to the invention, the hydrogel precursor solution can further include a cross-linked hydrophilic agent such as sodium alginate, pectin, chitosan, or (polyvinyl) alcohol; or a cell adhesive molecule such as fibronectin, laminin, vitronectin, or integrin binding peptide. In addition, the hydrogel of the invention can further include cells in the pores of the superporous hydrogel and/or one or more therapeutic agents.

The present invention also features a method for facilitating vascularization of a cell transplant by implanting a superporous hydrogel with cells encapsulated therein into a subject in need thereof thereby facilitating vascularization of the cell transplant.

DETAILED DESCRIPTION OF THE INVENTION

It has now been demonstrated that cells can be added to hydrogel precursor solutions and encapsulated within superporous hydrogel structures upon polymerization. Using the gas foaming method for producing superporous hydrogels, it was demonstrated that cell viability was not significantly affected by the precursor solution components, the sudden change in pH, foaming process, or gelation of the superporous hydrogels. The present invention is distinct from conventional methods in that the cells of the instant superporous hydrogels are encapsulated within the hydrogel matrix rather than only in the pores of the macroporous structure. Cell encapsulation within superporous scaffolds offers significant advantages. Encapsulation ensures a uniform distribution of cells within the scaffolds and allows for the analysis of heterotypic cell interactions within the porous space and the polymer space. In addition, the porous structure fosters vascularization conducive for cell survival and rapid vessel development. Moreover, the matrix allows the diffusion of cell-secreted albumin/insulin and also acts a mechanical barrier which prevents the contact of host cells and large immune system molecules. Thus, the superporous hydrogels of the invention find use in functional replacement of injured or damaged organs in the body.

Accordingly, the present invention provides superporous hydrogels with cells encapsulated within the hydrogel matrix and a method for producing the same. A superporous hydrogel, as used herein, refers to a semisolid three-dimensional structure which is capable of absorbing a substantial amount of water in a very short period of time due to the presence of a plurality of inter-connected macropores. A superporous hydrogel is characterized by having superabsorbence properties and mechanical strength.

In the dehydrated state, a superporous hydrogel of the invention has an average pore size in the range of 10 µm-3,000 µm, more preferably 50 µm-1,000 µm, and most preferably 100 µm-600 µm. In addition, the superporous hydrogel of the invention has a porosity in the range of 50 to 90%, more preferably 60 to 80% or most preferably 65 to 75%. Pore size can be modulated by a number of factors including, e.g., the nature of the solvent or solvents in which the gel is formed and/or the amount of polymerization initiator or catalyst.

Given the porosity of the instant hydrogels, swelling is rapid. In this respect, swelling of a dehydrated superporous hydrogel of the invention can reach equilibrium in, e.g., phosphate-buffered saline (PBS) in less than one minute and can swell to 90% of equilibrium weight within 2 to 5 minutes, or more preferably 3 minutes. In addition, superporous hydrogels of the invention had an equilibrium swelling ratio (Q), e.g., calculated according to the expression: $Q=W_s/W_d$, where $W_s$ is the weight of the swollen hydrogel and $W_d$ is the weight of dry hydrogel, in the range of 10 to 20, or more preferably 12 to 18. In other words, the superporous hydrogel of the invention can swell from 10 to 20 times its dry weight.

Superporous hydrogels are composed of polymers that will swell without dissolving when placed in water or other biological fluids. Hydrogels can generally absorb a great deal of fluid and, at equilibrium, typically are composed of 60-90% fluid and only 10-30% polymer. Hydrogels are particularly useful due to the inherent biocompatibility of the cross-linked polymeric network (Hill-West, et al. (1994) *Proc. Natl. Acad. Sci. USA* 91:5967-5971). Hydrogel biocompatibility can be attributed to hydrophilicity and ability to imbibe large amounts of biological fluids (Brannon-Peppas. *Preparation and Characterization of Cross-linked Hydrophilic Networks in Absorbent Polymer Technology*, Brannon-Peppas and Harland, Eds. 1990, Elsevier: Amsterdam, pp 45-66; Peppas and Mikos. *Preparation Methods and Structure of Hydrogels in Hydrogels in Medicine and Pharmacy*, Peppas, Ed. 1986, CRC Press: Boca Raton, Fla., pp 1-27). Also, hydrogels closely resemble the natural living extracellular matrix (Ratner and Hoffman. *Synthetic Hydrogels for Biomedical Applications in Hydrogels for Medical and Related Applications*, Andrade, Ed. 1976, American Chemical Society: Washington, DC, pp 1-36).

Hydrogel matrices of the invention are composed of synthetic hydrophilic macromers or polymers which have been synthetically produced and which are hydrophilic, but not necessarily water-soluble. Examples of synthetic hydrophilic polymers of use in the practice of the present invention are polyethylene glycol (PEG); polyoxyethylene; polymethylene glycol; polytrimethylene glycols; polyvinylpyrrolidones; poly(acrylic acid); poly(itaconic acid); poly(methacrylic acid); poly(hydroxypropyl acrylamide) (HPMA); poly(peptides) such as polyglutamate, polylysine, polyaspartate, polyserine, polythreonine, polycysteine; and polyoxyethylene-polyoxypropylene block polymers; and copolymers, and derivatives and mixtures thereof. While natural marine biopolymers such as agarose, chitosan, and alginate are also embraced by the present invention, in some embodiments, the hydrophilic matrix is not a naturally occurring polymer such as a protein, starch, cellulose, heparin, or hyaluronic acid.

Although different synthetic hydrophilic polymers and selected biopolymers can be used in connection with forming the hydrophilic matrix of the invention, the polymer must be biocompatible and hydrophilic, but cross-linked physically or chemically to prevent dissolution. Particularly suitable polymers include the various forms of derivatized PEG which are extensively used in the modification of biologically active molecules because they lack toxicity, antigenicity, and immunogenicity; have a wide range of solubilities; are generally non-biodegradable and are easily excreted from most living organisms including humans.

Poly(ethylene glycol)diacrylate (PEGDA) hydrogels have been widely accepted in many biomedical applications (Peppas, et al. (1999) *J. Controlled Release* 62:81-87). PEGDA hydrogels are hydrophilic, biocompatible, nontoxic, and exhibit variable mesh size depending upon PEG macromer length. As exemplified herein, superporous hydrogels produced from PEGDA are not toxic to cells and can be readily produced using the gas foaming method. Accordingly, particular embodiments of the present invention embrace superporous hydrogels produced with PEGDA.

Superporous hydrogels of the invention can be modified to possess high mechanical strength by incorporating cross-linked hydrophilic agent like sodium alginate, pectin, chitosan, (polyvinyl) alcohol that can cross-link after the matrix is formed (Omidian, et al. (2006) *Macromol. Biosci.* 6:703-10). Hydrogels can also be made degradable in vivo by incorporating PLA, PLGA or PGA polymers. Moreover, superporous hydrogels can be modified with cell adhesive molecule such as fibronectin, laminin, vitronectin, and an integrin binding peptide such as RGD to promote cell adhesion and proliferation (Heungsoo Shin (2003) *Biomaterials* 24:4353-4364; Hwang, et al. (2006) *Tissue Eng.* 12:2695-706).

Superporous hydrogels can also be modified with functional groups for covalently attaching a variety of compounds including therapeutic agents. Therapeutic agents which can be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix can be via a protease sensitive linker or other biodegradable linkage.

Other compounds which can be added to the superporous hydrogel matrix include, but are not limited to, vitamins and other nutritional supplements; glycoproteins; fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents. Therapeutic agents can be incorporated into the hydrophilic matrix of the invention to deliver therapeutically effective doses of the disclosed agents according to doses well-known in the art.

In addition to functional groups, the polymers of the instant hydrogels can further contain a means for controlled biodegradation to facilitate removal of the matrix polymer from the subject being treated. For example, PEGDA hydrogels can be made to biodegrade at a faster rate by modification (Sawhney, et al. (1994) *J. Biomed. Mater. Res.* 28:831-838). PEGDA hydrogels can be made biodegradable by incorporating a biodegradable cross-linker or by utilizing biodegradable copolymers (Sawhney, et al. (1993) *Macromolecules* 26:581-587; Park, et al. *Biodegradable Hydrogels for Drug Delivery.* 1993, Lancaster, Pa.: Technomic Pub. ix, 252; Watanabe, et al. (2002) *Biomaterials* 23:4041-4048; Yamini, et al. (1997) *J. Macromol. Sci.* A34:2461-2470). For example, telechelic biodegradable block copolymers, specifically degraded by either plasmin or crude collagenases, have been used in cross-linked hydrogels (West, et al. (1999) *Macromolecules,* 32:241-244). The extent and rate or degradation is controlled by the specific degradation mechanism used thereby limiting accumulation of the matrix at the site of implantation.

Hydrogels of the invention are produced by conventional gas foaming methods, wherein a hydrogel precursor solution is prepared and a foaming agent is added thereto to produce a foam, which gels or polymerizes to form a matrix with a plurality of macropores dispersed therein. A precursor solution is defined as the mixture of components which are combined to produce the superporous hydrogel structure, but lacks a foaming agent which facilitates foam formation and gelling or polymerization of the hydrogel. A precursor solution of the invention can include, but is not limited to, a macromer, an initiator, and a foam stabilizer. As disclosed herein, any suitable macromer can be employed with particular embodiments embracing the use of PEGDA.

A suitable foam stabilizer should be able to stabilize the foam until the beginning of the gelling process. Various surfactants, such as TRITON surfactants, TWEEN and SPAN surfactants, PLURONIC surfactants (poly(ethylene oxide)-poly(propylene oxide)-poly(ethylene oxide) tri-block copolymers) (BASF), SILWET surfactants (OSi Specialties Inc.), sodium dodecyl sulfate (Bio-Rad Laboratories), albumin (Sigma Chemical Company), and gelatin can be employed. However, in certain embodiments, the foam stabilizer of the invention includes one or more PLURONIC surfactants such as F127 or P105. In particular embodiments the foam stabilizer is PLURONIC F127.

In accordance with the method for producing a superporous hydrogel of the invention, cells are combined with the hydrogel precursor solution prior to gelation or polymerization. Advantageously, the hydrogels of the present invention can provide a greater number of viable cells compared to nonporous hydrogels. For example, as demonstrated herein, SPHs retained $2 \times 10^5$ viable NIH-3T3 cells after one week, whereas nonporous hydrogels retained $10^5$ viable cells. Cells of particular use in this invention include, but are not limited to, stem cells, fibroblasts, insulin-producing islet cells, hepatocytes, myocytes, neurons, chondrocytes, skin cells, bone marrow cells, and the like. In particular human mesenchymal stem cells (hMSCs) can be readily harvested from bone marrow aspirates from a patient and, under the appropriate conditions, have been shown to differentiate into multiple cell lineages that resemble osteoblasts, chondrocytes and adipocytes (Pittenger, et al. (1999) *Science* 284:143). MSCs can also differentiate into non-mesenchymal cells such as pulmonary epithelium (Kotton, et al. (2001) *Development* 128:5181), kidney epithelium (Herrera, et al. (2004) *Int. J. Mol. Med.* 14:1035), myocytes (Wakitani, et al. (1995) *Muscle Nerve* 18:1417), cardiomyocytes (Fukuda (2005) *Circ. J.* 69:1431) and neuronal cells (Phinney & Isakova (2005) *Curr. Pharm. Des.* 11:1255). MSCs have been successfully used to aid the healing of critical-sized skeletal defects in many animal models, including mice, rats, rabbits, swine, goats and sheep (Cowan, et al. (2005) *Curr. Top. Dev. Biol.* 66:239). Additionally, use of allogenic MSCs for repair of bone defects can be done without immunosuppressive therapy since MSCs do not express MHC Class II molecules required to fully activate T cells responsible for graft rejection (Arinzeh (2005) *Foot Ankle Clin.* 10:651).

In this respect, the cells can be autogenic, allogenic or xenogenic with respect to the subject receiving the instant cell-encapsulated superporous hydrogel. Cells can be isolated from biopsy samples or generated by differentiation and expansion of stem cells using conventional methods. For example, since MSCs account for a very small fraction of the total population of nucleated cells (0.001%-0.01%) within the marrow (Pittenger, et al. (1999) supra), in vitro osteogenic expansion and differentiation of MSCs has been well studied (Pittenger, et al. (1999) supra; Yang, et al. (2005) *Biomateri-* als 26:5991; Bruder, et al. (1997) *J. Cell Biochem.* 64:278; Jaiswal, et al. (1997) *J. Cell biochem.* 64:295).

In addition to being encapsulated within the hydrogel matrix, some embodiments embrace encapsulation of cells within the hydrogel pores as well. Cells encapsulated within the hydrogel matrix and hydrogel pores can be the same or different. For example, one could encapsulate stem cells in the hydrogel matrix and encapsulate cells capable of producing growth or differentiation factors in the pores, or vice versa.

To encapsulate the cells into the hydrogel matrix, a foaming agent is added to the cells and hydrogel precursor solution thereby producing a superporous hydrogel with cells encapsulated therein. As exemplified herein, a suitable foaming agent can be a chemical or physical foaming agent. In some embodiments, the foaming agent is sodium bicarbonate. In other embodiments, the foaming agent is a gas, e.g., compressed air or nitrogen. Other foaming agents of use in the gas foaming method are known to those of skill in the art.

As demonstrated herein, the components and fabrication method of the invention is not toxic to cells and enables encapsulation of cells within superporous hydrogels. In addition, the superporous hydrogel of the invention facilitates vascularization in vivo. As such, the hydrogels of the invention find application as biological scaffolds for maintaining and growing cells and in the functional replacement of injured or damaged organs of the body. In particular embodiments, the instant superporous hydrogel is used in the preparation of a variety of formed implants for use in medical applications. Advantageously, the superporous hydrogel is designed to provide cells to a damaged or injured site to facilitate regeneration and vascularization. Accordingly, the instant composition is useful for providing localized delivery of cells to a subject in need of such treatment and facilitating vascularization of the cell transplant. Such delivery can be used to, e.g., promote wound healing and in tissue regeneration or replacement, including bone tissue engineering. In particular embodiments, the hydrogels of the present invention are used in tissue engineering or regenerative medicine, as a model organ system for drug testing, or for use in cell expansion.

Depending on the application, the superporous hydrogel of the invention can be used alone or in admixture of a pharmaceutically acceptable carrier in a pharmaceutical composition. Suitable formulations for use in the present invention are found in Remington: The Science and Practice of Pharmacy, Alfonso R. Gennaro, editor, 20th ed. Lippincott Williams & Wilkins: Philadelphia, Pa., 2000. Exemplary carriers include, e.g., water, saline, alcohol, a buffer and the like. The compositions can also contain pharmaceutically acceptable auxiliary substances as required to approximate physiological conditions, such as pH adjusting and buffering agents, tonicity adjusting agents, wetting agents, detergents and the like.

The compositions of the invention can be formulated for any appropriate manner of administration, including for example, topical, intracranial implantation, subcutaneous implantation or intramuscular implantation depending on the site at which cells are to be delivered and the disease or condition be treated.

The invention is described in greater detail by the following non-limiting examples.

Example 1

Materials & Methods

PEGDA (MW 3400 Da) was purchased form Glycosan Biosystems (Salt Lake city, Utah). Ammonium persulphate (APS) and N,N,N',N'-tetramethylethylenediamine (TEMED) were purchased from Acros Chemicals (Morris Plains, N.J.). Citric acid was purchased from Spectrum Chemicals. PLURONIC® (F-127) was purchased from Sigma (St. Louis, Mo.). Sodium bicarbonate and sodium hydroxide were purchased from Fischer Scientific (Pittsburgh, Pa.). LIVE/DEAD cell viability assay kit (Gaugain, et al. (1978) *Biochemistry* 17:5071-8; Gaugain, et al. (1978) *Biochemistry* 17:5078-88) was purchased from Molecular Probes (Carlsbad, Calif.). CELLTITER 96® AQ$_{ueous}$ non-radioactive cell proliferation assay (MTS assay) (Mosmann, (1984) *J. Immunol. Methods* 65:55-63) was purchased from Promega (Madison, Wis.). QUANT-IT™ PICOGREEN® dsDNA assay kit (Singer, et al. (1997) *Anal. Biochem.* 249:228-38) was purchased from Molecular Probes (Carlsbad, Calif.). NIH-3T3 cells (fibroblasts derived from *Mus musculus*) and β-TC cells (pancreatic β-cells derived from *Mus musculus* and transgenic for SV40 large T antigen) were obtained from American Type Culture Collection (Manassas, Va.). DMEM, trypsin, EDTA, DPBS, DPBS with Ca and Mg, penicillin/streptomycin, and glutamine were obtained from Mediatech (Manassas, Va.).

Instruments. UV plate reader from Thermo Labsystems Multiskan Plus (Milford, Mass.) was used to record absorbance. Fluorescence plate reader from Spectra Max Gemini XS (Ramsey, Minn.) was used to record fluorescence intensity. A fluorescent microscope from Olympus IX70 (Center Valley, Pa.) was used to record fluorescence images of cells. Software used for image analysis was IP labs (Germany) and the camera used for capturing images was Retiga 1300 Cooled Mono 12-bit CCD manufactured by Q-Imaging (Canada). Scanning electron microscope from Hitachi S-3000N (Brisbane, California) was used in characterizing superporous hydrogels.

Statistical Analysis. Data from all the studies was analyzed using One-way ANOVA followed by Unpaired Student's t-test. All results are reported as mean±standard deviation. To confirm the reproducibility of the data, three identical and independent studies were performed. Statistical analysis was performed within studies but not across studies to identify differences between groups.

Synthesis of Superporous Hydrogels (SPH). Stock solutions of PEGDA (MW 3400 Da), APS, TEMED, F-127, and citric acid were prepared as follows. A 30% (w/v) stock solution of PEGDA (MW 3400 Da) was prepared by adding 1.5 grams of PEGDA to 5 mL of DPBS with Ca and Mg. A 20% (w/v) stock solution of APS was prepared by adding 0.50 gram of APS to 2.5 mL of DPBS with Ca and Mg. A 20% (w/v) stock solution of TEMED was prepared by adding 0.50 gram of TEMED to 2.5 mL of DPBS with Ca and Mg. A 10% (w/v) stock of F-127 was prepared by adding 0.25 gram of F-127 to 2.5 mL of DPBS with Ca and Mg. A 20% (w/v) stock of citric acid was prepared by adding 0.50 gram of citric acid to 2.5 mL of DPBS with Ca and Mg.

Using the above-referenced stock solutions, superporous hydrogels were prepared. Specifically, 250 µL PEGDA (MW 3400 Da), 30 µL PLURONIC F-127, 22.5 µL TEMED, and 20 µL citric acid were combined in a 4 mL vial (h=4-6 cm, d=1.2 cm) and the solution was vortexed to obtain a homogenous mixture. APS (17.5 µL) was added to the homogenous mixture, which was again vortexed to mix uniformly. This solution was heated to 37-40° C. in a water bath for 2 minutes with intermittent vortexing of the vial. NIH-3T3 cells (2×10$^6$ cells/mL) or β-TC cells (10$^6$ cells/mL) suspended in DPBS were added to the vial to achieve a final volume of 160 µL. The vial was gently vortexed and a pH of 5.0 was confirmed. Sodium bicarbonate (100 mg) was immediately added to the vial and a steel spatula was used to uniformly disperse the foam generated upon addition of the sodium bicarbonate. The SPH was allowed to stand for 5 minutes in the vial for complete polymerization. A wet spatula was used to remove the SPH, which was subsequently immersed in a beaker containing 25 mL of medium (modified DMEM). The SPH was allowed to swell in the medium for 30 minutes.

Synthesis of Non-porous Gels. Preparation of non-porous gels was same as indicated for porous gels; however, to make non-porous gels sodium bicarbonate was substituted with (10 µl of 5M NaOH).

Preparation of SPH with Cell Adhesive Peptides. Cell adhesive peptides with integrin-binding sequence, acryl-GRGDSG (SEQ ID NO:1), and the scrambled sequence acryl-GDGRSG (SEQ ID NO:2) as a control (Hubbell (1995) *Biotechnology* (NY) 13:565), were dissolved in the precursor solution at a concentration of 2.5 mM and the remaining procedure for hydrogel preparation followed to give adhesive RGD-PEGDA SPHs and the expectedly non-adhesive DGR-PEGDA SPHs, respectively. Acryl-GRGDSG (SEQ ID NO:1) and acryl-GDGRSG (SEQ ID NO:2) were custom synthesized by solid phase peptide synthesis (Protein Research Laboratory, University of Illinois at Chicago) where acryl-G indicates an acrylated group added to the amino terminal using succinimide chemistry. The concentration of 2.5 mM was chosen based upon the previously reported capacity of PEGDA hydrogels containing 1.25 mM to 2.5 mM RGD peptide within the hydrogels to promote osteogenesis in MSCs (Yang, et al. (2005) supra). Incorporation of the peptides within the hydrogel was determined using fluorescein-conjugated versions of the peptides and found to be 67 to 70% by fluorescent spectroscopy and confirmed by mass spectrometry. At this incorporation level (1.67-1.75 mM), the RGD density would correspond to 1.675 pmol $RGD/cm^2$-as determined for 10 nm of the hydrogel surface being available for interaction with cells (Elbert & Hubbell (2001) *Biomacromolecules* 2:430), which is well above the biologically relevant RGD density of 1 fmol $RGD/cm^2$ required for cell spreading and 10 fmol $RGD/cm^2$ that is reported to be required for formation of focal adhesion (Massia & Hubbell (1991) *J. Cell. Biol.* 114:1089) although this is expected to vary for different cell types.

Swelling. Superporous hydrogels were prepared without cells. After swelling the gels for 30 minutes in media, the SPH was dehydrated in 80% alcohol overnight. Subsequently, superporous hydrogels were dehydrated in 100% alcohol for at least 4 hours and then moved to a food desiccator where the SPH were dried at 58° C. for 1 hour for complete drying. Intermittent rolling of the gels ensured uniform drying.

The swelling ratio of SPH was determined by dipping the SPH in PBS buffer at 37° C. for 30 seconds. The weight of the swelled hydrogel was recorded. The hydrogel was returned to the PBS for another 30 seconds and the weight was recorded. This procedure was repeated multiple times for 30 seconds each for a total of 5 minutes. Additional measurements were taken every 5 minutes for a total of 1 hour and again at 24 and 48 hours.

Effect of Hydrogel Precursor Solution Components on Cell Viability. Cells ($10^5$ cells/mL) were plated on 48-well plates and were allowed to adhere to the plates overnight. Two stock solutions of PEGDA 50% (w/v) were prepared by weighing 0.5 grams of PEGDA in 1000 µL of DPBS with Ca and Mg. The pH of one solution was adjusted to 5 (using 1 M NaOH) and that of the other solution was adjusted to 8 (using 1 M NaOH). Cells were treated with 5% to 30% (w/v) PEGDA at pH 5 for 10 minutes. Cells were treated 5% to 30% (w/v) PEGDA at pH 8 for 24, 48, and 72 hours. The treatment groups were compared to untreated controls where cells were incubated with media. PEGDA was aspirated from cells at the above-referenced time points, washed with DPBS (containing Ca and Mg), and resuspended in fresh media. To this, 30 µL of MTS test reagent was added. Cells were then incubated with MTS test reagent for 3 hours and absorbance recorded at 490 nm on a UV plate reader.

LIVE/DEAD cell assay was used to visualize live and dead cells (Gaugain, et al. (1978) *Biochemistry* 17:5071-8; Gaugain, et al. (1978) *Biochemistry* 17:5078-88). Cells were prepared and treated with PEGDA as above. To the resuspended cells was added 100 µL of calcein-AM/ethidium homodimer stain (stock solutions of the dyes were prepared as per manufacturer's protocol-Molecular Probes). Cells were incubated for 30 minutes and images were captured of both treatment and control groups using a fluorescence microscope.

Analysis of the other components of the hydrogel precursor solution was conducted as described for PEGDA. Specifically, cells were treated with 0.05% to 1.5% (w/v) APS at pH 5 for 10 minutes or 0.05% to 1.5% (w/v) APS at pH 8 for 24, 48, or 72 hours and compared to controls in a MTS test and LIVE/DEAD cell assay. Similarly, cells were treated with 0.05% to 0.90% (w/v) TEMED at pH 5 for 10 minutes or 0.05% to 0.90% (w/v) TEMED at pH 8 for 24, 48, or 72 hours and compared to controls in a MTS test and LIVE/DEAD cell assay. Likewise, cells were treated with 0.05% to 1.0% (w/v) F-127 at pH 5 for 10 minutes or 0.05% to 1.0% (w/v) F-127 at pH 8 for 24, 48, or 72 hours and compared to controls in a MTS test and LIVE/DEAD cell assay. Analysis of citric acid was similarly carried out, wherein cells were 0.25% to 3% (w/v) citric acid at pH 5 or 0.25% to 3% (w/v) citric acid at pH 8 for 24, 48, or 72 hours and compared to controls in a MTS test and LIVE/DEAD cell assay.

Cell viability determinations in the presence of sodium bicarbonate were likewise performed. For analysis at pH 5.0, cells were treated with media at pH 5.0 and then sodium bicarbonate was added to each well. Specifically, 10 mg to 250 mg of sodium bicarbonate powder was added per ml of cells and the cells were allowed to incubate for 10 minutes. Treatment of cells at pH 8 for 24, 48 and 72 hours was carried out in 10 mg/mL to 250 mg/mL of sodium bicarbonate. Treatment groups were compared to untreated controls in both a MTS test and LIVE/DEAD cell assay.

Cell viability in the presence of saturated sodium bicarbonate was also analyzed. A saturated solution of sodium bicarbonate was prepared by adding 100 mg sodium bicarbonate to 1 mL media (the pH of which was adjusted to 5). On addition of sodium bicarbonate, the pH of the solution increased and became alkaline. The suspension in the test tube was allowed to stand for 5 minutes. Cells were treated with the supernatant for 10 minutes or 24, 48, or 72 hours. The saturated solution was aspirated from the wells, cells were washed and analyzed with the MTS test and LIVE/DEAD cell assay.

Effect of pH on Cell Viability. Cells ($10^5$ cells/mL) were plated on 48 well plates and were allowed to adhere to the plates overnight. Cells were treated with media adjusted to pH 3, 4, 5, 6, 7, 8 and 9 for 10 minutes, 24 hours, 48 hours, or 72 hours. Media was aspirated and cells were washed and analyzed by the MTS test or LIVE/DEAD cell assay.

To determine whether abrupt changes in pH had an effect on cell viability, cells ($10^5$ cells/mL) were suspended in media at pH 5, wherein one group was treated with 100 mg/mL of sodium bicarbonate and another group was treated with 5M NaOH to cause a change from acidic to alkaline pH. A third group was the untreated controls. At the end of 10 minutes, the cells were washed, resuspended in fresh media, and analyzed with the MTS test reagent and LIVE/DEAD cell assay.

Effect of Gas Foaming on Cell Viability. Cells ($10^5$ cells/mL) were suspended in media containing the precursor solution used in fabrication of superporous hydrogels. In the precursor solution, PEGDA was replaced with PEG to prevent the gelation of the precursor solution. In brief, the procedure followed was PEG (MW 4000 Da), DPBS with Ca and Mg, F-127, TEMED, citric acid, APS and cell suspension were combined and pH was adjusted to 5. Subsequently, sodium bicarbonate was added to each well and cells were incubated with the precursor solution for 10 minutes. The treatment groups were compared to untreated controls, which had equivalent amount of DPBS with Ca and Mg during the treatment period. Two additional groups were also studied. One group of cells was treated as described above, however, the sodium bicarbonate was substituted with 10 µl of 5M NaOH, a quantity sufficient to make the solution alkaline. In the second group, PEG plus IRGACURE (0.15% (w/v)) and cells were exposed to UV 5 mW/cm$^2$ for 10 minutes. After all treatments, cells were washed twice and were resuspended in fresh media for analysis via the MTS test and LIVE/DEAD cell assay Effect of Chemical Foaming on Cell Viability. Chemical foaming using photopolymerization (i.e., IRGACURE® 2959 {4-(2-hydroxyethoxy)phenyl-(2-hydroxy-2-propyl)ketone} incorporation followed by exposure to light at wavelength of 265 nm) was analyzed. Cells ($10^5$ cells/mL) were suspended in media and treated with a precursor solution containing PEG, F-127, IRGACURE and citric acid. The precursor mix containing cells was exposed to UV at 5 mW/cm$^2$ for 2.5 minutes and sodium bicarbonate was added. The precursor solution containing cells was subsequently exposed to UV for another 3 minutes, washed twice and analyzed via the MTS test and LIVE/DEAD cell assay. In another group, cells were treated in the same manner, however, the sodium bicarbonate was substituted with 10 µL of 5 M NaOH, a quantity sufficient to make the solution alkaline.

Effect of Physical Foaming on Cell Viability. Cells ($10^5$ cells/mL) were suspended in media and treated with the precursor solution used in fabrication of superporous hydrogels. In the precursor solution PEGDA was replaced with PEG to prevent the gelation of the precursor solution. In brief, PEG, F-127, and IRGACURE were combined in a fine Buchner funnel (Pore size: 4-5 µm, Pyrex No. 36060) and pH was determined to be around 7-8. The precursor solution was then exposed to UV for 3.5 minutes. In one treatment group nitrogen gas/compressed air was applied to the top of the cells at 200 psi for 2 minutes at a flow rate of 4000 mL/minute. In a second treatment group, nitrogen gas/compressed air was applied from below the cells suspended in the Buchner funnel at 200 psi for 2 minutes at a flow rate of 4000 mL/minute. Thereafter, each of the groups was exposed to UV at 5 mW/cm$^2$ for 3 minutes, washed twice with DPBS containing Ca and Mg, resuspended in fresh media and transferred to a 48-well plate. Cells were incubated for 24, 48 and 72 hours and cell viability was determined via the MTS test and LIVE/DEAD cell assay.

Cell Viability of Cells Encapsulated Within SPH for Extended Periods of Time. QUANT-IT™ PICOGREEN® dsDNA was used in the detection of DNA from live cells (Singer, et al. (1997) *Anal. Biochem.* 249:228-38). Superporous hydrogels were synthesized with NIH-3T3 as described herein and placed in 6-well plates. Similarly, non-porous hydrogels were prepared as described herein and placed in 6-well plates. Cells plated on 6-well plates were used as positive controls. Cell viability was tested at 24 hours, 48 hours, 72 hours and 1 week. At the end of each of these incubation periods, media was aspirated off and the cells were lysed using a probe sonicator. DNA test reagent was added to each well and the plate was incubated for 15 minutes with shaking. Fluorescence intensity was recorded on spectramax fluorescence plate reader at excitation of 480 nm and emission of 520 nm. The fluorescence signal from hydrogels without cells (blank) was subtracted from corresponding hydrogels containing the cells. Cell viability was extrapolated from a standard curve of cells encapsulated within the non-porous hydrogels containing $10^4$ to $1.5 \times 10^6$ NIH-3T3 cells/gel ($R^2$=0.9837). The gels used for generation of standard curve were prepared in the same way as that of SPH, however the sodium bicarbonate in the formula was substituted with NaOH.

LIVE/DEAD assay was used as a qualitative assay to determine the cell viability. Non-porous hydrogels and superporous hydrogels were synthesized with NIH-3T3 cells as described herein and placed in 6-well plates. Cells plated on 6-well plates were used as positive controls. Cell viability was tested at 24 hours, 48 hours, 72 hours and 1 week by aspirating off media and adding calcein-AM/ethidium homodimer stain premixed in DPBS. Cells were incubated for 30 minutes and images were captured for both treatment and control groups using a fluorescence microscope.

As with NIH-3T3 cells, viability of β-TC cells was determined at 24 hours, 48 hours, 72 hours and 1 week after encapsulation within superporous hydrogels. Cell viability was extrapolated from the standard curve of cells encapsulated within the non-porous hydrogels containing $5 \times 10^3$ to $5 \times 10^5$ β-TC cells/gel ($R^2$=0.9914). A LIVE/DEAD assay was also performed to qualitatively determine the cell viability of β-TC cells.

MSC Isolation and seeding. Human MSCs were isolated from whole bone marrow aspirates according to published methods (Alhadlaq, et al. (2005) *Tissue Eng.* 11:556). MSCs from two different donors, up to passage four, were used for all the experiments. For cell seeding, the SPHs were placed in 48 well plates. The MSCs were harvested using 0.25% trypsin with 1M EDTA, centrifuged and resuspended in basal medium. This cell suspension, corresponding to a final cell number of $2.5 \times 10^5$ cells in approximately 40 µL of medium, was then added drop-wise to each of the SPHs. The hydrogels were placed in the incubator for fifteen minutes to allow equilibrium swelling. Thereafter, 1 mL of corresponding medium was added to each of the wells, and the plates were incubated at 37° C. in 5% $CO_2$. Basal medium was composed of Dulbecco's modified Eagle's medium (DMEM) supplemented with 10% fetal bovine serum, 100 unit/mL penicillin and 100 µg/mL streptomycin. osteogenic medium was composed of basal medium with 100 nM dexamethasone, 10 mM β-glycerophosphate and 0.05 mM ascorbic acid 2-phosphate (Pittenger, et al. (1999) supra). Osteogenic medium treatment was started 24 hours post-seeding. The distribution of cells within the hydrogels was observed by sectioning each hydrogel into three equal discs along the height with a scalpel.

MSC viability, measured as a function of mitochondrial activity, was determined by modified MTT assay. The SPHs were placed in a 48 well plate and cell suspensions at appropriate cell density were seeded drop-wise onto the SPHs. The volume of DPBS used to prepare the cell suspensions was normalized for all the cell densities. To every well, 200 µL of DPBS and 40 µL of reagent were then added directly. The plates were covered and incubated at 37° C. for two hours. At the end of two hours, 100 µL of the supernatant was transferred to a new plate and read at a wavelength of 490 nm (Labsystems Multiskan Plate Reader). A standard curve was obtained by plotting the linear relationship between the cell number seeded and the absorbance value obtained. The controls for background absorbance were acellular SPHs in DPBS and empty wells To determine the incorporation efficiency within the SPHs immediately after seeding, the SPHs were transferred to new well-plates to exclude any cells that were not intimately interacting with the surface or entrapped within the SPH. The remainder of the procedure for the assay was as described herein. Incorporation efficiency (%) was calculated as the absorbance of the sample divided by absorbance of the standard (cells added directly to the SPH and not moved to a new multi-well plate) multiplied by 100.

For determining the viability of MSCs seeded within the SPHs at various time intervals, the hydrogel samples were transferred to new multi-well plates-to remove cells adherent to the plate- and rinsed with DPBS to remove any serum components. Each SPH was then incubated with 200 µL of DPBS and 40 µL of reagent for two hours, at the end of which 100 µL of the supernatant was transferred to a new plate and absorbance determined. Based on the standard curve previously obtained, the corresponding cell number for a given absorbance was determined.

At various time points, cell stains were used to visualize the cells within the pores of the hydrogels. Calcein AM was used to visualize live cells (Lichtenfels, et al. (1994) *J. Immunol. Methods* 172:227). Actin staining (Cooper (1987) *J. Cell Biol.* 105:1473) was achieved by fixing cells with 4% paraformaldehyde followed by staining with ALEXA FLUOR 546 PHALLOIDIN® and Hoechst 33258 dye was used to visualize the nucleus (Latt & Stetten (1976) *J. Histochem. Cytochem.* 24:24).

Human Umbilical Vein Endothelial Cells (HUVECs) Seeding and Viability. HUVECs (BD™ Biosciences) were cultured in endothelial cell growth medium (EGM-2) at 37° C. in 5% $CO_2$ and used between passages 1 and 5. The procedures for cell seeding and cell viability measurements were similar as those for described for MSCs. A standard curve with HUVECs was also developed.

In Vitro Mineralization. Hydrogels were transferred to serum-free medium 24 hours before collection to minimize serum components present within the hydrogels. Alkaline phosphatase (ALP) levels were determined by the formation of p-nitrophenol (Eaton (1977) *Clin. Chem.* 23:2148), and was performed as per manufacturer's protocol (QUANTICHROM™ Alkaline Phosphatase assay kit, BioAssay Systems). Calcium was determined by complexation of calcium by a phenolsulphonephtalein dye (Woo & Cannon (1984) *Metabolic Intermediates and Inorganic Ions*, J B Henry R M, editor, Philadelphia, pp 133) (QUANTICHROM™ Calcium assay kit, BioAssay Systems). Briefly, the lyophilized hydrogels were homogenized with 1 mL of 0.5 N HCl and mixed overnight at 4° C. The supernatant was used for calcium assays, as per manufacturer's protocol. Separate hydrogels were fixed with 4% paraformaldehyde and the von Kossa staining technique (Sheehan & Hrapchak (1980) *Theory and Practice of Histotechnology*, St. Louis, C.V. Mosby Co.) was used to visualize matrix mineralization.

Scanning Electron Microscopy and Energy Dispersive Spectroscopy. Dried hydrogel samples were cut using a scalpel and dehydrated. Energy dispersive X-ray spectroscopy (EDS; Oxford Inca) was performed on sections of the dried hydrogels taken from different locations within the porous structure of the SPHs to study the atomic composition of the deposited calcium. At least nine random locations in three independent SPHs were examined for each SPH and condition. Following EDS analysis, samples were sputter coated with gold/palladium for scanning electron microscopy (SEM; Hitachi S-3000 N) imaging. Scanning electron microscopy was used to investigate surface and interior morphology of the dried sections. Using MATLAB 6.1 (The MathWorks, Inc., Natick, Mass.), the SEM image was transformed to a binary image with the isodata threshold algorithm (Ridler & Calvard (1978) IEEE Transactions on Systems, man and Cybernetics, SMC-8, 630), which calculates the best threshold value out of the gray value histogram of the image. The binary image had two phases, the 'solid' phase composed of the hydrogel scaffold and the 'pore' phase. Porosity was calculated as the ratio of the total number of pixels in the pore phase to the total number of pixels in the entire image. SEM images of dried section were used to gather information on the pore size distribution. To obtain the pore size distribution within hydrated SPHs, dried hydrogel sections were hydrated with PBS and allowed to swell to equilibrium following which the hydrated section was gently tapped on paper towels to remove excess PBS and observed under bright field. Images were used measure pore size within a fully hydrated SPH.

Data Analysis. All data was expressed as a mean plus or minus (±) the standard deviation and were compared using one-way ANOVA with subsequent post hoc test. Differences at p-value less than or equal to 0.05 were considered to be statistically significant. All error bars were presented as standard deviations.

Example 2

Characterization of Superporous Hydrogels

Swelling. Superporous hydrogels were characterized by determining the swelling ratio. By capillary driven absorption, the superporous hydrogels reached equilibrium swelling within seconds. SPHs swelled to 90% of equilibrium weight within 3 minutes, indicating that the superporous structure is highly interconnected. Swelling of superporous hydrogels was also expressed as a swelling ratio (q), which is the total wet weight at time, t, per dry weight. Superporous hydrogels had an equilibrium swelling ratio of approximately 14 (n=3), swelling to 14 times their dry weight within 5 minutes. These results confirm their superporous nature (Gemeinhart & Park (2000) *Polymers Adv. Technol.* 11:617-625).

Scanning Electron Microscopy. Many techniques have been used for generation of nano and micro topographies on hydrogel scaffolds. Some of these techniques, e.g., electron beam lithography, generates pore structures greater than 3 to 5 nm for a single feature and ≧30-40 nm for arrays of features; polymer-polymer demixing generates features ≧13 nm; colloidal lithography generates features ≧20 nm and is dependent on etchant used and time; electrospinning generates features ≧3 nm; phase separation generates features ≧1 nm; photolithography (near-UV) generates ≧0.5 nm (Norman & Desai (2006) *Ann. Biomed. Eng.* 34:89-101); and solvent/particulate leaching generates features 250-500 µm (Liao, et al. (2002) *J. Biomed. Mater. Res.* 59:676-81). The superporous hydrogels produced using the methods disclosed herein had an interconnected pore network with pore sizes ranging from 100 to 600 µm. The porosity of the SPHs was found to be 71±2.1%. The pore size range of the hydrated SPH, estimated from bright field images, was within the same range but slightly larger pores were observed. There was a broad distribution in the pore size with the hydrated SPHs having a larger pore diameter and broader distribution in pore diameter, 395±107 µm, than the dehydrated SPH, 250±94 µm. These sizes were similar to those previously reported for superporous hydrogels in both the dehydrated and hydrated states (Gemeinhart, et al. (2000) *J. Biomater. Sci. Polym. Ed.* 11:1371). The interconnected nature of the pores and rapid pore filling was expected to contribute to uniform distribution of cells within the SPH.

Example 3

Effect of Precursor Solution Components of SPH on Cell Viability

The effects of precursor solution constituents on cell viability were analyzed over a 72 hour period. The experiments were designed based on the conditions that the cells would be exposed to during the fabrication of superporous hydrogels; i.e., exposure to each constituent of SPH individually at pH of 5 for 10 minutes and thereafter for 24, 48 and 72 hours at pH of 8. CELLTITER 96 AQUEOUS ONE® solution Cell Proliferation Assay (MTS) and LIVE/DEAD cell assay were used to determine the effect of each of the constituents on cell viability.

Effect of PEGDA (MW 3400 Da). There was little toxicity observed when cells were treated with different concentrations of PEGDA (5 to 30%) for 10 minutes. However, there was significant toxicity observed at all concentrations when cells were incubated for 24 hours, 48 hours and 72 hours. The two lower concentrations of PEGDA (5 and 10%) exhibited a higher number of viable cells and beyond 15% there was significant cell death when incubated over longer periods of time. The concentration of PEGDA used in superporous hydrogels is typically 15%. At 15% PEGDA, there were 78.1±7.5% viable cells at the end of 10 minutes. At the end of 24 hours, 48 hours and 72 hours there were 27.4±0.8%, 25±8.8%, and 19.39±13.3% viable cells, respectively. There was a statistically significant difference in cell viability at 15% of PEGDA at 10 minutes, 24 hours, 48 hours and 72 hours compared to untreated controls. Thus, PEGDA macromers over prolonged periods of time were toxic to cells. It was important to determine the effect of the macromer solution or unpolymerized PEGDA because during polymerization 100% of the PEGDA macromers do not undergo gelation, there is generally some amount of PEGDA that remains unpolymerized and may be harmful to cells encapsulated therein. Most of the cells were alive at 10 minutes for all the concentrations of PEGDA tested, as determined by LIVE/DEAD cell assay. However, at higher concentrations, the morphology of cells changed and the cell number was reduced. After incubation for 24, 48 and 72 hours with macromer solution, the images showed that all cells were dead. While it has been suggested that PEGDA macromers are non-toxic (Bhadra, et al. (2002) *Pharmazie* 57:5-29), it has been shown that osteoblasts photoencapsulated within nonporous PEGDA gels containing 20% or 30% PEGDA had a significantly higher cell death compared to non-porous gels containing 10% PEGDA on day 1, 1 week and 2 weeks (Burdick & Anseth (2002) *Biomaterials* 23:4315-23).

Effect of TEMED. TEMED is an initiation catalyst and as a redox couple with APS (Allcock, et al. (2003) *Contemporary Polymer Chemistry*, Pearson Education Inc.). It is protonated at an acidic pH and is active only at an alkaline pH, accelerating the generation of free radicals by APS. There was no significant toxicity when cells were treated with 0.05% to 0.90% TEMED for 10 minutes; there were viable cells at all concentrations of TEMED after treatment for 10 minutes. However, there was toxicity observed at all concentrations when cells were incubated for 24 hours, 48 hours and 72 hours as determined by MTS assay. The concentration of TEMED used in fabrication of SPH is typically 0.90%. At the end of 10 minutes in the presence of 0.90% TEMED, there were 108.59±1.23% viable cells. In contrast, there were 30.63±5.51%, 20.41±6.92%, 18.53±12.82% viable cells at the end of 24 hours, 48 hours and 72 hours. There was a statistically significant difference in cell viability at 0.90% TEMED at 10 minutes, 24 hours, 48 hours and 72 hours compared to untreated controls. The results from the LIVE/DEAD cell assay confirmed results from the MTS assay. For all the concentrations of TEMED tested at 10 minutes, cells were alive and when cells were incubated for longer time periods, they were dead. Moreover, there was a change in morphology observed when cells were incubated for longer periods of time at all concentrations of TEMED tested.

It has been shown that APS/TEMED, each at a concentration of 10 mM or 15 mM, had no toxicity on marrow stromal cells (Betz, et al. (Nov. 2007) *J. Biomed. Mater. Res. A*). In contrast, significant toxicity was reported at 20 mM at the end of 3 hours. Because APS/TEMED were tested simultaneously, the toxicity observed at 20 mM may have be due to APS and not TEMED.

Effect of APS. TEMED at an alkaline pH accelerates the generation of free radicals by APS, which results in gelation of the macromer solution. APS was toxic to cells at all concentrations tested (0.05% to 1.5%) for 10 minutes, 24 hours, 48 hours and 72 hours. The concentration of APS used in SPH is generally 0.70%. There were 21.25±9.6%, 16.83±4.8%, 14.8±6.8%, 11.63±0.3% viable cells at the end of 10 minutes, 24 hours, 48 hours and 72 hours, respectively, incubation period with 0.70% APS. The difference in cell viability at 0.70% APS at each time period was statistically significant compared to untreated controls. APS causes the release of free ionic radicals, which may be the cause of cytotoxicity. Since free radicals can react with many different cellular macromolecules (including cell membranes, proteins, and DNA) and cause cellular damage, an understanding of the effects these radicals may have on cells is important. The images from LIVE/DEAD cell assay showed dead cells at the end of each of the incubation periods. Cells were balled up when incubated with 0.05 to 1.5% APS over 72 hours. While 60% cell viability was observed at 0.05% APS, the LIVE/DEAD cell assay indicated that the cells were dead. This may have been due to damage to the cell membrane which allowed the penetration of the ethidium homodimer within the cell, but did not fully reduce all metabolic activity detected by MTS assay.

The concentration of APS used in fabrication of the SPH herein was 30 mM, which is higher than the concentrations conventionally employed (Betz, et al. (2007) supra). Since there was significant toxicity observed at 30 mM APS, lower concentrations of APS were used for synthesis of SPH. However, at lower concentrations of 10 mM to 16 mM, synthesize of SPH was limited since foaming and gelation did not occur simultaneously.

Cytocompatibility of various UV initiators like 2,2-dimethoxy-2-phenylacetophenone (IRGACURE 651), 1-hydroxycyclohexyl phenyl ketone (IRGACURE 184), 2-methyl-1-[4-(methylthio)phenyl]-2-(4-morpholinyl)-1-propanone (IRGACURE 907), 2-hydroxy-1-[4-(hydroxyethoxy)phenyl]-2-methyl-1-propanone (DAROCUR 2959) and visible light initiating systems such as caSPHorquinone (CQ), ethyl 4-N,N-dimethylaminobenzoate (4EDMAB) in presence of triethanolamine (TEA), the photosensitizer isopropyl thioxanthone with NIH-3T3 cells have been examined. All of these initiators at concentrations of <0.01% w/w were cytocompatible for 10 minutes with the exception of CQ, Darocur 2959 and 4EDMAB (Bryant, et al. (2000) *J. Biomater. Sci. Polym. Ed.* 11:439-57). The most promising UV photoinitiator studied for cytocompatibility was D2959, at concentrations <0.05% (w/w), light intensities of 6 mW/cm$^2$ at 365 nm light and polymerization times up to 10 minutes. CQ was the most promising visible light photoinitiator studied. In another study, the cytotoxicity of 2-hydroxy-1-[4-(hydroxyethoxy) phenyl]-2-methyl-1-propanone (IRGACURE 2959) was examined for six mammalian cell lines (human fetal osteoblasts, bovine chondrocytes, corneal epithelial cells, human mesenchymal stem cells, goat mesenchymal stem cells, and human embryonic germ cells). It was observed that IRGAUCRE 2959 at a concentration from 0.03 to 0.1% was well tolerated by a wide variety of mammalian cell lines (Williams, et al. (2005) *Biomaterials* 26:1211-8).

Effect of Citric Acid. The pH during SPH fabrication is acidic to retard the polymerization of the macromers until the time the foaming process is initiated. In this regard, citric acid is used to adjust the pH to 5 during the fabrication of SPH. There was a slight toxicity to cells incubated with 1.8% and 3% citric acid for 10 minutes at pH of 5. Cell death was observed at all the concentrations of citric acid when cells were incubated for longer periods of time with citric acid. The concentration of citric acid used in SPH is typically at about 2.4%. After 10 minutes in 2.4% citric acid, there were about 99.7±11.6% viable cells. At the end of 24 hours, 48 hours, and 72 hours there were 28.95±5.70, 15.81±1.80, and 16.20±6.81% viable cells, respectively, when treated with 2.4% citric acid, as determined by MTS assay. Differences in cell viability in the presence of 2.4% citric acid for 10 minutes, 24 hours, 48 hours and 72 hours was statistically significant compared to untreated controls. The pH of the medium was adjusted to 8 when cells were treated with citric acid over the 24, 48, and 72 hour periods. However the pH could not be maintained at 8 because incubation with citric acid over longer periods of time causes the pH to drop. This acidic pH may be the cause of cell death after 72 hours. The results from LIVE/DEAD cell assay confirmed the results obtained from MTS assay; cells were alive when incubated with 0.25% to 3% citric acid for 10 minutes, but died when incubated with 0.25% to 3% citric acid for up to 72 hours.

It has been demonstrated that 47.6 mM citric acid (pH 2.3) in water leads to complete cell death within three minutes of incubation (Lan, et al. (1999) *Aust. Dent. J.* 44:123-30). Media containing 23.8 mM and 47.6 mM citric acid exerted strong cytotoxicity (47% to 90% cell death) and also inhibited protein synthesis (IC$_{50}$=0.28%) in gingival fibroblasts within three hours of incubation. Incubation of cells in medium containing 11.9 mM citric acid also suppressed the attachment and spreading of fibroblasts on culture plates and Type I collagen, with 58% and 22% of inhibition, respectively (Lan, et al. (1999) supra). However, there was no cell death observed when cells were treated with citric acid at concentrations of 13 mM to 150 mM for 10 minutes. The reason for this variation was because the pH of the medium containing citric acid was adjusted to 5. Hence, incubation for a shorter time was not toxic to cells. However, when cells were incubated for longer periods of time with citric acid, the pH did not remain at 5, dropping to a highly acidic pH which was toxic to cells.

Effect of F-127. F-127 is used as a foam stabilizer. It stabilizes the foam generated during the formation of SPH and prevents it from collapsing. The concentration of F-127 used in SPH is typically 0.6%. At the end of 10 minutes, 24 hours, 48 hours, and 72 hours there were 94.6±4.81%, 107.4±1.4%, 116.7±4.3%, and 114.93±18.13% viable cells, respectively, when treated with 0.6% F-127 as determined by MTS assay. There was no toxicity observed at any concentration of F-127 over 72 hours. The results from LIVE/DEAD cell assay confirmed the results observed in the MTS assay. All the cells were alive at all concentrations of F-127 tested at the end of each of the incubation periods.

These results are consistent with observations that F-127 is not toxic to cells and promotes proliferation of cells at concentrations of 0.1% and 5% for 5 days (Khattak, et al. (2005) *Tissue Eng.* 11:974-83).

Effect of Sodium Bicarbonate. Sodium bicarbonate has two functions; creating an alkaline pH where TEMED becomes active and facilitating foaming of the precursor solution to give SPH its porous structure. There was a significant amount of toxicity at concentrations greater than 100 mg/mL at 10 minutes, 24 hours, 48 hours, and 72 hours. However, at concentrations less than 100 mg/mL, there was no toxicity observed at 10 minutes but significant toxicity at 24 hours, 48 hours, and 72 hours. The concentration used in the preparation of SPH is typically 200 mg/mL. At 10 minutes, there were 58.54±0.22% viable cells in the presence of 200 mg/mL sodium bicarbonate, where as at 24, 48 and 72 hours there was a significant drop in the cell viability to 31.93±10.83%, 22.50±3.9, and 22.35±4.06%, respectively, as determined by MTS assay. There was a significant difference in the cell viability at 10 minutes, 24 hours, 48 hours and 72 hours compared to untreated controls. Moreover, cells were dead when treated from 50 to 250 mg/mL of sodium bicarbonate crystals for up to 72 hours. After 10 minutes, cells were predominantly alive at sodium bicarbonate concentrations above 100 mg/mL. Indeed, it has been shown that at concentrations of 25, 50 and 100 mM sodium bicarbonate, cell viability is not affected for up to 6 hours (Hirsch & Haller (2004) *Eur. J. Med. Res.* 9:71-7).

Effect of a Saturated Solution of Sodium Bicarbonate. Cells were also treated with a saturated solution of sodium bicarbonate. This analysis was conducted because cells can be exposed to a saturated solution of sodium bicarbonate, wherein excess sodium bicarbonate crystals can settle down or be washed away during the fabrication of superporous hydrogels. There was no significant toxicity when cells were treated with a saturated solution of sodium bicarbonate. At 10 minutes, 24 hours, 48 hours and 72 hours there were 100.81±1.73%, 96.10±0.55%, 96.63±3.755%, and 99.855±2.08% viable cells, respectively. Moreover, cells were alive at the end of 72 hours as determined by the LIVE/DEAD cell assay.

Example 4

Effect of pH on Cell Viability

During the fabrication of SPH, cells are exposed to pH 5 (pH of the precursor solution) and thereafter to pH 8 conditions. Thus, to determine how this change in pH affects cells viability, cells were exposed to various pHs. There was no significant toxicity when cells were treated with media from pH 4 to 9 for 10 minutes. Media at pH 3 had a cytotoxic effect on cells; cell viability fell to about 61.84±2.81% after treatment for 10 minutes. At 10 minutes, 24 hours, 48 hours and 72 hours, there were 100.91±1.80%, 82.87±2.30, 24.35±5.35%, and 17.24±8.88% viable cells, respected, when treated with media at pH 5 as determined by MTS assay. At pH 8 there was no significant toxicity observed at the end of any of the incubation periods tested. The results from LIVE/DEAD cell assay confirmed the MTS assay results.

During the fabrication of SPH cells are first exposed to pH 5 and, upon addition of sodium bicarbonate, there is a sudden change in pH from an acidic to a highly alkaline pH. Therefore, the effect of a sudden change in pH was also evaluated.

In both treatment groups, a pH change due to sodium bicarbonate and pH change due to sodium hydroxide caused a significant amount of cell death as determined by MTS and LIVE/DEAD cell assays.

Example 5

Effect of Gas Foaming on Cell Viability

The gas foaming technique is used for fabrication of SPH. Gas foaming agents are classified as physical and chemical foaming agents. Nitrogen and carbon dioxide are physical foaming agents that expand when pressure is released, resulting in formation of a cellular structure in the polymer. Chemical foaming agents include compounds that react or decompose to form gas upon exposure to reagents or environmental conditions. Chemical foaming agents are typically preferred over physical foaming agents due to the difficulty of obtaining a homogeneous blend and controlling the high gas pressure and diffusion rate of gas when utilizing physical foaming agents (Park (1998) Super absorbable hydrogel foams. Purdue Research Foundation: USA).

Therefore, the effect of both chemical and physical foaming agent on cell viability was determined. PEGDA was substituted with PEG to prevent polymerization of the precursor solution. Cells were exposed to exactly the same conditions and constituents as that during the fabrication of superporous hydrogels. Cells were studied in suspension in order to expose them to the same interface they would be exposed to during the fabrication of superporous hydrogels.

To analyze the effect of chemical foaming via sodium bicarbonate, one treatment group of cells was treated with the precursor solution used in fabrication of SPH. In a second treatment group, the precursor solution used in fabrication of non-porous hydrogels was prepared with the same formula as SPH but containing sodium hydroxide instead of sodium bicarbonate. Precursor solution containing PEG plus IRGACURE 2959, PEG alone, and UV treatment groups served as control groups. There was a significant cell death in the treatment groups. There was approximately 70% cell death when cells were treated with precursor solution used in fabrication of SPH and approximately 50% cell death with the precursor solution of corresponding non-porous hydrogels, i.e., hydrogel formed without foaming. Thus, there was toxicity due to the composition of the superporous gels and some amount of additional cell death was due to the foaming process. The images from the LIVE/DEAD assay correlated with the results of MTS assay; there were significant numbers of dead cells in both the treatment groups.

As an alternative to the APS/TEMED initiator system, IRGACURE® 2959 (4-(2-hydroxyethoxy)phenyl-(2-hydroxy-2-propyl) ketone) was incorporated into the SPH precursor solution followed by exposure to light at wavelength of 265nm. It has been shown that IRGACURE 2959 at concentrations of 0.3-0.1% are not associated with toxicity (Williams, et al. (2005) *Biomaterials* 26:1211-8). Non-porous gels synthesized from 10% PEG derivatives and 0.05% IRGACURE 2959 supports the growth and proliferation of human mesenchymal stem cells (Nuttelman, et al. (2004) *J. Biomed. Mater. Res. A* 68:773-82; Nuttelman, et al. (2006) *Biomaterials* 27:1377-86). Photopolymerized PEG-based hydrogels (containing IRGACURE) have also been successfully used for growth and chondrogenic differentiation of embryonic stem cells (Hwang, et al. (2006) *Tissue Eng.* 12:2695-706). The concentration of IRGACURE used in the analysis herein was based on conventional concentrations of IRGACURE 2959. A significant amount of cell death was observed when cells were treated with precursor solution containing PEG, IRGACURE under UV irradiation, citric acid, F-127 and sodium bicarbonate/sodium hydroxide. There was approximately 70% cell death when cells were treated with the precursor solution and precursor solution used for fabricating non-porous hydrogels with sodium hydroxide. However, when cells were treated with IRGACURE 2959 alone as a positive control, there were approximately 90% viable cells. Thus, the cell death may be associated with the sudden pH change. LIVE/DEAD cell assay showed significant cell death.

Accordingly, as an alternative to sodium bicarbonate, a novel gas foaming technique was used in which the pH of the precursor solution is maintained at pH 7-8 (Park (1998) supra). Nitrogen gas under pressure or compressed air was used instead of sodium bicarbonate for generation of foam. Nitrogen gas under pressure or compressed air are physical foaming agents. There was approximately 20% cell death compared to untreated controls when cell viability was determined immediately after treating cells with nitrogen gas under pressure or compressed air. There was no statistically significant difference in cell viability determined immediately after treating cells with compressed air or nitrogen gas under pressure. This study was further extended and cells subjected to foaming were washed and plated on cell culture plates for 24, 48 and 72 hours. The cell viability was studied at the end of each of the above incubation periods. It was observed that at the end of 24, 48 and 72 hours there was no significant difference in the cell viability when nitrogen gas or compressed air were blown on top of the cells or blown from below to generate the foam. However, there was cell death observed over 72 hours when nitrogen gas under pressure was used for foam generation. There was no cell death observed over 72 hours when compressed air was used for generation of foam. The percentage of cell survival when compressed air was used for foaming at 24 hours, 48 hours and 72 hours was higher and statistically significant compared to the corresponding treatment groups where nitrogen gas under pressure was used for foaming. The images from LIVE/DEAD cells assay indicated that all cells were alive when compressed air was used for foaming.

Example 6

Cell Viability after Encapsulation within the SPH Matrix

To determine the viability of cells encapsulated within superporous hydrogels and nonporous gels, QUANT-IT™ PICOGREEN® dsDNA and LIVE/DEAD cell assays were used for both NIH-3T3 cells and β-TC. The picogreen reagent binds to dsDNA by either intercalating with dsDNA or via groove interactions with dsDNA. It is speculated that the picogreen reagent may be sensitive to the conformation of the dsDNA (Singer, et al. (1997) *Anal. Biochem.* 249:228-38). DNA as a biomarker was used to determine the number of viable cells, since DNA fragmentation is a hallmark in apoptosis (Liao, et al. (2002) *J. Biomed. Mater. Res.* 59:676-81; Saraste & Pulkki (2000) *Cardiovasc. Res.* 45:528-37; Darzynkiewicz, et al. (1997) *Cytometry* 27:1-20). At the same time DNA fragmentation also occurs in cell death due to necrosis. Multiple assays were employed to determine the cell viability when cells were encapsulated within the non-porous gels. Some of these assays included MTS assay (PROMEGA), MTT assay (PROMEGA), MultiTox-Fluor Multiplex Cytotoxicity Assay, CELLTITER-GLO® Luminescent Cell Viability Assay, CELLTITER-BLUE® Cell Viability Assay, CYTOTOX-ONE™ Homogeneous Membrane Integrity Assay, and Vybrant Cytotoxicity Assay. Most of these assays could accurately detect cells seeded on hydrogels; however, none of these assays could determine the cell viability when cells were encapsulated within the nonporous hydrogels. In some assays the background signal from the hydrogels was too high, whereas other assays failed to interact with the cells when encapsulated within the hydrogel matrix.

To evaluate cell viability when cells were encapsulated within SPH, gels were synthesized using PEGDA-macromer, APS/TEMED-initiator system, citric acid-pH adjustment to 5, F-127-foam stabilizer and sodium bicarbonate as foaming agent. This formula for studying the cell viability after encapsulation of cells within SPH was used because this system has been optimized and extensively studied for seeding cells on SPH. NIH-3T3 cells were encapsulated within the superporous hydrogels. At the end of 24 hours there were approximately $10^6$ viable cells/SPH, which over 1 week declined to approximately $2 \times 10^5$ viable cells/SPH. This cell death may have occurred due to toxicity of APS/sodium bicarbonate, foaming technique, change in pH of the precursor solution from acidic to alkaline during fabrication of gels or encapsulation of cells within the gels. For non-porous hydrogels prepared with the same formula as SPH; however, containing sodium hydroxide instead of sodium bicarbonate, approximately $10^6$ cells/gel were detected at the end of 24 hours, a number which declined to $10^5$ cells/gel over 1 week. The cause of cell death in the non-porous hydrogels may be due to toxicity of the constituents of non-porous gels, pH change effect of the precursor solution or due to encapsulation of cells within the gels. There was no cell death observed in non-porous hydrogels prepared with IRGACURE/UV initiator system. Therefore, it appeared that cell death was due to the composition of the hydrogels and technique used in fabrication of the hydrogels, e.g., sudden pH change. The images obtained from LIVE/DEAD cell assays indicated that there were significant amount of cells alive in both non-porous hydrogels and superporous hydrogels over 72 hours. However, the images at 1 week showed that a considerable number of cells were dead. Thus, NIH-3T3 cells did not survive for more than 72 hours when encapsulated within the SPH.

A non-porous scaffold utilizing PEGDA and the APS/TEMED initiator system has been described (Betz, et al. (2007) supra), which supports the growth and proliferation of encapsulated bone stromal cells. Non-porous hydrogels (EH-PEG) containing a macromer solution of cyclic acetal-based biomaterial and poly(ethylene glycol)diacrylate (PEGDA) were formed by free radical polymerization initiated by ammonium persulfate (APS) and N,N,N',N'-tetramethylethylenediamine (TEMED), each used at a concentration of 15 mM. It was shown that EH-PEG hydrogels were a viable option for encapsulation and osteodifferentiation of BMSCs (Betz, et al. (2007) supra). Differences between the results presented herein and those of the prior art may be attributed to differences in initiator concentrations. In addition, the method for preparation of non-porous hydrogels does not appear to employ any pH change (acidic to basic) of the precursor solution. As seen above, APS (initiator) and pH change may be two important factors leading to cell death.

To determine whether cell survival within the SPH was cell-line dependent, the pancreatic β cell line β-TC was encapsulated within the SPH matrix. The total number of cells encapsulated within the superporous hydrogels was interpolated from the standard curve of cells encapsulated within the non-porous gels. There was a drop in cell viability when cells were encapsulated within superporous hydrogels as well as non-porous hydrogels. The cell viability in superporous hydrogels fell from $1.5 \times 10^5$ cells/gel at 24 hours to $3.4 \times 10^4$ cells/gel at the end of 1 week. Cell viability in non-porous hydrogels dropped from $2.5 \times 10^5$ cells/gel at 24 hours to $6 \times 10^4$ cells/gel at the end of 1 week. The images from the LIVE/DEAD cell assay showed significant numbers of dead cells at 24, 48, 72 hours and 1 week. In conclusion, β-TC cells do not survive over 24 hours in either non-porous or superporous hydrogels, likely due to changes in pH and the initiator system employed.

Example 7

Cell Seeding and Distribution in PEGDA Hydrogel Pores

Following cell seeding of the SPHs by drop-wise addition of cell suspension to the dehydrated hydrogels, MSC incorporation efficiency was found to be 89%±3.5% of the total number of cells that were dropped onto the scaffold. The method of cell seeding employed was capable of delivering cells throughout the SPH. The cells were all viable and few (no more than 5 per frame of view) dead-membrane disrupted-cells were observed immediately after seeding. MSCs were distributed widely in each of the sections with qualitatively similar distribution.

To support this, NIH/3T3 cells were observed across a full radial section at the axial center of a SPH. Cells were present throughout the section and at the very center of the SPH. Qualitatively, the cells appeared to be randomly distributed; however, there appeared to be non-homogeneous distribution in the sections. More detailed localization experiments are performed to confirm this, but the results clearly showed that there were cells present in the interior and throughout the pores of the SPH immediately after seeding. To gain some quantitative understanding of the distribution of cells in the pores of the SPHs, eight sectors (4 from the top half of the SPH and 4 from the bottom) were examined for uniformity of loading (Table 1). Depending upon the exact loading conditions, the sections were found to be statistically equivalent (p=0.069).

TABLE 1

| | Percent of the total cells loaded (mean ± standard deviation %) | | | |
|---|---|---|---|---|
| | 1 | 2 | 3 | 4 |
| Top | 13.32 ± 1.96 | 11.31 ± 0.73 | 12.31 ± 2.08 | 10.18 ± 0.40 |
| Bottom | 14.58 ± 1.57 | 12.68 ± 1.16 | 12.76 ± 1.39 | 12.86 ± 1.60 |

Cells ($7.5 \times 10^5$ cells) were seeded on the top of the hydrogel by drop-wise addition in approximately 40 μL of cell suspension (n = 3). Each cylindrical hydrogel was cut in half by height and each half of the hydrogel further sectioned into four identical radial sections.

Example 8

MSC Survival and Viability in the Pores of PEGDA Hydrogels

Cells penetrated into the interior of the SPHs and concentrated around the edges of the pores within the SPHs. The hMSCs appeared to attach to the hydrogel and stained positive for the presence of actin filaments, indicating cell-matrix interactions. While cells seeded within the pores of the PEGDA SPHs were seen present with native, spread morphology, cells seeded on top of non-porous, unmodified PEGDA hydrogels did not survive culture or populate the hydrogel surfaces. In comparison, nonporous RGD-PEGDA hydrogels, enabled stem cell survival. Within the PEGDA SPHs, cells were viable for a period of over 30 days. No significant difference was observed between the capacity of PEGDA SPHs and adhesive RGD-PEGDA SPHs to support stem cell growth. MSCs grown on the RGD-containing nonporous hydrogels were able to maintain a high cell count while MSCs on peptide-free nonporous hydrogels rapidly died.

The cell number was determined using the linearity of the modified MTT assay for the range of cells seeding used in this study. Similar standard curves were obtained for NIH/3T3 cells and HUVECs seeded within the pores of PEGDA SPHs, with $R^2$ values of 0.93 and 0.97, respectively. Unlike DNA quantification methods that do not discriminate between DNA from dead cells or live cells (Ahn, et al. (1996) *Nucl. Acid Res.* 24:2623), the modified MTS assay is a cell viability assay and a more accurate predictor of the number of cells within the SPH that are available for further populating the SPH. Cells were also encapsulated within PEGDA hydrogels and PEGDA SPHs and no correlation was obtained between modified MTT absorbance and cell number at time points ranging from immediately after encapsulation to 48 hours.

Example 9

HUVECs Survival in PEGDA Hydrogels

Unlike the hMSCs, which remained viable in the pores of unmodified PEGDA SPHs, HUVECs needed the adhesive RGD peptide for survival in SPHs. HUVECs seeded on RGD-PEGDA SPHs proliferated to a relative cell count 69.8±4.5% greater than HUVECs seeded on PEGDA SPHs, and DGR-PEGDA SPHs did not survive with a relative cell count drop to 11.98±1.63% ($p<0.01$ compared to RGD-PEGDA NPH) and 7.87±0.5% ($p<0.0001$ compared to RGD-PEGDA NPH), respectively, of the seeded cells. This observation was not only in agreement with behavior of HUVECs on modified polymers (Lin, et al. (1992) *Biomaterials* 13:905), but also confirmed that the cell adhesive peptides incorporated within the PEGDA SPHs were biologically active.

Example 10

In Vitro Mineralization

PEGDA SPHs, RGD-PEGDA SPHs, and DGR-PEGDA SPHs cell-seeded constructs were cultured in DMEM basal medium and osteogenic medium. Cells in the pores of the SPHs, upon exposure to osteogenic medium or basal medium, remained viable over the entire duration of the study. Even after 7 weeks of culture, the cells were found concentrated around the pores and throughout the porous structure. Gross visible calcification could be observed by the end of week 3, and by week 7 the exterior of the osteogenic samples were predominantly white from mineralization. The visual mineralization was confirmed by Von Kossa staining of the same SPHs.

Following 3 weeks of culture, a two-fold increase in ALP level was observed for hMSCs cultured in osteogenic medium compared to hMSCs cultured in basal medium. Peak ALP levels at week 3 coincided with the start of calcium matrix production within the SPHs cultured in osteogenic medium. Deposited calcium levels were low at week 3 and increased through weeks 5 and 7. By the 5th week, expression levels of ALP in the osteogenic samples were similar to the expression levels of ALP in basal medium samples, as would be expected with the osteogenic differentiation process (Lian & Stein (1992) *Crit. Rev. Oral Biol. Med.* 3:269). All PEGDA SPHs incubated in osteogenic medium showed calcification throughout the matrices with depositions having calcium to phosphate (Ca/P) ratios ranging from 1.51 to 1.56 for all groups. The stoichiometric Ca/P ratio for pure hydroxyapatite $[Ca_{10}(PO_4)_6(OH)_2]$ is 1.67. However, bone is composed of both hydroxyapatite and calcium deficient hydroxyapatite, thus creating a composite Ca/P ratio around 1.60 in bone (Bronzino (2006) *Tissue Engineering and Artificial Organs*, Boca Raton, Fla. CRC/Taylor & Francis).

Acellular PEGDA SPHs respond to the osteogenic microenvironment by calcium deposition within the SPHs. Increased levels of calcium were observed in all the acellular groups with the highest levels in unmodified PEGDA SPHs although, this increase was similar to calcium levels in cellular constructs cultured in basal medium. Overall, the levels of automineralization in PEGDA SPHs by week 3 (3.15±2.83 μg/mg dry weight) were much lower in comparison to those previously reported in PEGDA nonporous hydrogels (28.7±1.34 μg/mg dry weight for 10% PEGDA nonporous hydrogels and 32.3±2.50 μg/mg dry weight for 20% PEGDA nonporous hydrogels)(Wang, et al. (2005) *Tissue Eng.* 11:201) for the same time frame. The acellular SPH groups also served to elucidate the contribution of stem cell driven mineralization toward the calcium content detected within the MSC-seeded SPH groups cultured in osteogenic medium.

Example 11

Vascular Ingrowth into Superporous Hydrogels

To further demonstrate the utility of the SPHs of the present invention, it was determined whether the highly interconnected porous architecture would be favorable for cellular infiltration and angiogenesis in vivo. PEGDA (MW 3400 g/mol) SPH scaffolds were prepared and characterized as described herein. Briefly, PEGDA solution, foam stabilizer (Pluronic® F127, double distilled water, the initiator pair, N,N,N',N'-tetramethylethylene-diamine (TEMED) and ammonium persulfate, were added sequentially to a glass vial. Saturated citric acid solution was used for pH adjustment. The precursor solution was mixed and heated gently to 37° C. for approximately 2 minutes. Sodium bicarbonate, 200 mg, was added with constant stirring to evenly distribute the salt and evolving gas. The SPHs were then removed from the vial and allowed to swell in double distilled water to remove traces of unpolymerized monomers and salt before dehydrating in 80% ethanol followed by overnight dehydration in absolute ethanol. The hydrogels were then dried in a food dessicator and stored in an airtight container for further use. To make the non-porous PEGDA hydrogels (NPH), sodium bicarbonate, 200 mg, was replaced with sodium hydroxide solution. The precursor solution was pipetted into 96 well plates with each well containing an equivalent volume to the size of the total volume of the porous hydrogel. Polymerization was allowed to proceed for half an hour. The NPHs were then rinsed with double distilled water to remove traces of unpolymerized monomers, dried and stored in an airtight container for further use. Scanning electron microscopy of the interior surface of the dehydrated SPHs revealed interconnected pores ranging from 100 μm to 600 μm with an average pore size of 250±94 μm. The hydrated SPH had a larger pore diameter and broader distribution in pore diameter, 395±107 μm, as estimated from bright field images.

To investigate the potential of the SPHs for in vivo angiogenesis, the SPHs were implanted in the dorsal skin fold of SCID mice (Fox Chase SCID, Charles River Laboratories). SCID mice were chosen as the model for vascularization as part of a larger experimental design involving human cells incorporated within the SPH where the tissue growth and vascularization within the SPH are evaluated. Experimental design for the study was developed using power analysis of published data of porous polymer implants (Arinzeh, et al. (2005) *Biomaterials* 26:3631-3638; Hidetsugu, et al. (2007) *J. Biomed. Sci.* 14:255-263). Briefly, the mice were divided into two groups of seven mice each. The mice were anesthetized with intraperitoneal injection of 100 mg/kg ketamine and 5 mg/kg xylazine. Subcutaneous pockets were opened in the back of the mice using an initial subcutaneous incision and a blunt probe. Two hydrogels, either SPH or NPH, were inserted within either side of the pocket. The incision was closed and the animals were monitored for four weeks. At the end of four weeks, the mice were sacrificed by an overdose of carbon dioxide followed by cervical dislocation. The hydrogels were removed en bloc. Fixed samples were placed in paraffin, sectioned and processed further for histological evaluation of cellular infiltration and vascular ingrowths.

Upon implantation, the hydrogels could be palpated easily. Daily monitoring did not reveal any weight loss or any apparent signs of toxicity like inflammation or reddening of skin in the test animals. At the end of four weeks, the hydrogels could be seen attached to the inside of the dorsal skin. Gross appearance revealed the red, vascularized superporous hydrogels and the pale yellow avascular non-porous hydrogels. Hematoxylin and eosin (H&E) staining of the SPH sections revealed host cell infiltration throughout the scaffold, which was absent in the nonporous hydrogels. Thus, the porous architecture of the SPH seemed to provide a favorable environment for micro-vessel formation. While it has previously been demonstrated that the rate and the depth of vascular ingrowths within scaffolds are influenced by the presence of pores (Gerecht, et al. (2007) *Biomaterials* 28:4826-4835) the number of vascular ingrowths are limited by the interconnectivity of the pores within the scaffolds (Druecke, et al. (2004) *J. Biomed. Mater. Res. A* 68:10-18; Landers, et al. (2002) *Biomaterials* 23:4437-4447).

To further elucidate the presence of host cells, paraffin embedded sections were de-paraffinized in xylene, hydrated with serial concentrations of ethanol and stained with Hoechst 33258 nuclear stain (Latt & Stetten (1976) supra). A fibrotic, vascularized capsular layer surrounding the SPH was formed. Extracted SPH implants showed the presence of blood cells and vascular structures. A representative image taken from the center of the SPH section revealed the presence of these ingrowths to the core of the SPH. Lumen-like structures filled with blood cells confirmed the presence of a functional microvasculature.

To further confirm the presence of microvasculature, CD34, an early stage endothelial cell marker (Civin, et al. (1990) *Prog. Clin. Biol. Res.* 333:387-401), and alpha smooth muscle actin (α-SMA), a vascular smooth muscle cell marker (Van Gieson, et al. (2003) *Circ. Res.* 92:929-936), were examined. Briefly, the de-paraffinized and hydrated sections were blocked with 1% bovine serum albumin in phosphate-buffered saline (pH 7.4) for 30 minutes. The sections were then incubated with primary rat polyclonal antibodies against CD34 and mouse polyclonal antibodies against smooth muscle α-actin (Santa Cruz Biotechnology) for 2 hours followed by incubation with FITC-conjugated goat anti-rat and goat anti-mouse (Molecular Probes), respectively, for 30 minutes. Hoechst 33258 was used as the nuclear stain. CD34-positive endothelial cells were localized throughout the SPHs. In addition, vessel lining musculature (Owens (1995) *Physiol. Rev.* 75:487-517) was observed in the form of α-SMA positive cells, associated with the vascular growths. These results indicate that the ingrowths observed within the implanted acellular SPHs are neo-vasculature.

What is claimed is:

1. A superporous hydrogel matrix produced by combining cells with a hydrogel precursor solution and initiator; and adding a chemical foaming agent, or compressed air or nitrogen, so that a superporous hydrogel having an average pore size of 10 to 3000 μm and a porosity of 50 to 90% is produced, wherein said superporous hydrogel matrix has cells encapsulated therein.

2. The superporous hydrogel matrix of claim 1, wherein the matrix comprises a synthetic hydrophilic polymer.

3. The superporous hydrogel matrix of claim 2, wherein the synthetic hydrophilic polymer is poly(ethylene glycol) diacrylate.

4. The superporous hydrogel matrix of claim 1, wherein the matrix comprises a foam stabilizer.

5. The superporous hydrogel matrix of claim 4, wherein the foam stabilizer comprises a (poly(ethylene oxide)-poly(propylene oxide)-poly(ethylene oxide) tri-block copolymer.

6. The superporous hydrogel matrix of claim 1, further comprising a cross-linked hydrophilic agent.

7. The superporous hydrogel matrix of claim 6, wherein the cross-linked hydrophilic agent is selected from the group of sodium alginate, pectin, chitosan, and (polyvinyl) alcohol.

8. The superporous hydrogel matrix of claim 1, further comprising a cell adhesive molecule.

9. The superporous hydrogel matrix of claim 8, wherein the cell adhesive molecule is selected from the group of fibronectin, laminin, vitronectin, and integrin binding peptide.

10. The superporous hydrogel matrix of claim 1, further comprising one or more therapeutic agents.

11. The superporous hydrogel matrix of claim 1, further comprising cells within the hydrogel pores.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 1

Gly Arg Gly Asp Ser Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 2

Gly Asp Gly Arg Ser Gly
1               5
```